US005662907A

United States Patent [19]
Kubo et al.

[11] Patent Number: 5,662,907
[45] Date of Patent: Sep. 2, 1997

[54] INDUCTION OF ANTI-TUMOR CYTOTOXIC T LYMPHOCYTES IN HUMANS USING SYNTHETIC PEPTIDE EPITOPES

[75] Inventors: Ralph T. Kubo, San Diego; Howard M. Grey; Alessandro Sette, both of La Jolla; Esteban Celis, San Diego, all of Calif.

[73] Assignee: Cytel Corporation, San Diego, Calif.

[21] Appl. No.: 186,266

[22] Filed: Jan. 25, 1994

Related U.S. Application Data

[63] Continuation-in-part of Ser. No. 159,339, Nov. 29, 1993, which is a continuation-in-part of Ser. No. 103,396, Aug. 6, 1993, abandoned, which is a continuation-in-part of Ser. No. 27,746, Mar. 5, 1993, abandoned, which is a continuation-in-part of Ser. No. 926,666, Aug. 7, 1992, abandoned.

[51] Int. Cl.$^6$ .............................. A61K 39/39; C07K 7/00
[52] U.S. Cl. ........................ 424/185.1; 424/193.1; 424/197.11; 424/277.1; 530/300; 530/328; 530/403
[58] Field of Search ................. 424/184.1, 185.1, 424/277.1, 197.11; 514/2, 12–16; 530/300, 324–328, 395, 806–7, 402–3

[56] References Cited

U.S. PATENT DOCUMENTS

| 5,200,320 | 4/1993 | Sette et al. ......................... 435/7.24 |
| 5,342,774 | 8/1994 | Boon et al. ......................... 435/240.2 |
| 5,405,940 | 4/1995 | Boon et al. ......................... 530/328 |

FOREIGN PATENT DOCUMENTS

WO94/05304  3/1994  WIPO.

OTHER PUBLICATIONS

Celis, E., et al., P.N.A.S. (USA) 91:2105–2109 (Mar., 1994), "Induction of anti–tumor cytotoxic T lymphocytes in normal humans using primary culture and synthetic peptide epitopes".

Ding, M., et al., Biochem. Biophys. Res. Comm. 202(1) 549–555 (Jul. 15, 1994), "Cloning and analysis of MAGE–1–related genes".

Gaugler, B., et al., J. Exp. Med. 179(3):921–930 (Mar. 1, 1994), "Human gene MAGE–3 codes for an antigen recognized on a melanoma by autologous cytolytic T lymphocytes".

Oaks, M. K., et al., Cancer Res. 54: 1627–29 (Apr. 1, 1994), "Molecular cytogenetic mapping of the human melanoma antigen (MAGE) gene family to chromosome region Xq27–qter: implications for MAGE immunotherapy".

Paul, W. F. (ed.), *Fundamental Immunology*, 3rd edition, pp. 976–978 (1993), Raven Press, New York.

Traversari, C., et al., J. Exp. Med. 176:1453–1457 (Nov., 1992), "A nonpeptide encoded by human gene MAGE–1 is recognized on HLA–A1 by cytolytic T lymphocytes directed against tumor antigen MZ2E".

*Robbins Pathologic Basis of Disease*, 4th edition (R.S. Cotran, et al., ed.), pp. 296–299 (1989), W.B. Saunders Co., Philadelphia.

Weynants, P., et al., Int. J. Cancer 56:826–29 (1994), "Expression of MAGE genes by non–small–cell lung carcinomas".

Zakut, R., et al., Cancer Res. 53:5–8 (Jan. 1, 1993), "Differential expression of MAGE–1, –2 and –3 messenger RNA in transformed and normal human cell lines".

Aichele, P et al., J. Exp. Med. 171:1815–1820 (May, 1990), "Antiviral cytotoxic T cell response induced by in vivo priming with a free synthetic peptide". May 1990.

Kast, W. M. et al., Proc. Nat'l Acad. Sci. 88:2283–2287 (Mar., 1991), "Protection against lethal Sendai virus infection by in vivo priming of virus–specific cytotoxic T lymphocytes with a free synthetic peptide". Mar. 1991.

Deres, K. et al., Nature 342:561–564 (30 Nov. 1989), "In vivo priming of virus–specific cytotoxic lymphocytes with synthetic lipopeptide vaccine". Nov. 30, 1989.

Traversari, C. et al., J. Exp. Med. 176:1453–1457 (Nov., 1992), "A nonapeptide encoded by human gene MAGE–1 is recognized on HLA–A1 by cytolytic T lymphocytes directed against tumor antigen MZ2–E". Nov. 1992.

*Primary Examiner*—Thomas M. Cunningham
*Attorney, Agent, or Firm*—Townsend and Townsend and Crew, LLP

[57] ABSTRACT

The present invention relates to compositions and methods for treating cancer. The invention provides peptides based on a 9 residue epitope derived from the product of the tumor-associated gene MAGE-3. The peptide induces CTL that kill melanoma and other tumor cells lines.

23 Claims, 2 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide ( x i ) SEQUENCE DESCRIPTION: SEQ ID NO:1:

Glu Ala Asp Pro Thr Gly His Ser Tyr
1               5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Glu Val Asp Pro Ile Gly His Leu Tyr
1               5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:3:

Tyr Leu Glu Pro Ala Ile Ala Lys Tyr
1               5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:4:

Glu Val Val Pro Ile Ser His Leu Tyr
1               5

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: peptide     ( i x ) FEATURE:
        ( A ) NAME/KEY: Peptide
        ( B ) LOCATION: 1..14
        ( D ) OTHER INFORMATION: /note= "Tetanus toxin at positions
            830-843."

( x i ) SEQUENCE DES (i i) MOLECULE TYPE: peptide (i x) FEATURE:
    (A) NAME/KEY: Peptide
    (B) LOCATION: 1..21
    (D) OTHER INFORMATION: /note= "Plasmodium falciparum CS
        protein at positions 378-398."

(x i) SEQUENCE DESCRIPTION: SEQ ID NO:6:

```
Asp Ile Glu Lys Lys Ile Ala Lys Met Glu Lys Ala Ser Ser Val Phe
1               5                   10                  15

Asn Val Val Asn Ser
            20
```

(2) INFORMATION FOR SEQ ID NO:7:

(i) SEQUENCE CHARACTERISTICS:
    (A) LENGTH: 17 amino acids
    (B) TYPE: amino acid
    (D) TOPOLOGY: linear (i i) MOLECULE TYPE: peptide (i x) FEATURE:
    (A) NAME/KEY: Peptide
    (B) LOCATION: 1..17
    (D) OTHER INFORMATION: /note= "Streptococcus 18kD protein
        at positions 1-16."

(x i) SEQUENCE DESCRIPTION: SEQ ID NO:7:

```
Tyr Gly Ala Val Asp Ser Ile Leu Gly Gly Val Ala Thr Tyr Gly Ala
1               5                   10                  15

Ala
```

(2) INFORMATION FOR SEQ ID NO:8:

(i) SEQUENCE CHARACTERISTICS:
    (A) LENGTH: 6 amino acids
    (B) TYPE: amino acid
    (D) TOPOLOGY: linear (i i) MOLECULE TYPE: peptide (i x) FEATURE:
    (A) NAME/KEY: Peptide
    (B) LOCATION: 1..5
    (D) OTHER INFORMATION: /note= "Peptide spacer."

(x i) SEQUENCE DESCRIPTION: SEQ ID NO:8:

```
Lys Ser Ser Ala Ala Ala
1               5
```

(2) INFORMATION FOR SEQ ID NO:9:

(i) SEQUENCE CHARACTERISTICS:
    (A) LENGTH: 32 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note= "The Lys at the N-terminus
        is lipadated using two palmitic acid residues."

(x i) SEQUENCE DESCRIPTION: SEQ ID NO:9:

```
Lys Ser Ser Ala Ala Ala Gln Tyr Ile Lys Ala Asn Ser Lys Phe Ile
1               5                   10                  15
```

```
Gly  Ile  Thr  Glu  Ala  Ala  Ala  Glu  Val  Asp  Pro  Ile  Gly  His  Leu  Tyr
          20                       25                       30
```

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 1
        ( D ) OTHER INFORMATION: /note= "Xaa at position 1 is
            D- alanine."

( i x ) FEATURE:
        ( A ) NAME/KEY: Modified-site
        ( B ) LOCATION: 3
        ( D ) OTHER INFORMATION: /note= "Xaa at position 3 is
            cyclohexylalanine."

( i x ) FEATURE:
        ( A ) NAME/KEY: Modified-site
        ( B ) LOCATION: 13
        ( D ) OTHER INFORMATION: /note= "Xaa at position 13 is
            D- alanine."

( x i ) SEQUENCE DESCRIPTION: SEQ ID NO:10:

```
Xaa  Lys  Xaa  Val  Trp  Ala  Asn  Thr  Leu  Lys  Ala  Ala  Xaa
1                   5                        10
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:11:

```
Glu  Tyr  Asp  Pro  Ile  Gly  His  Leu  Tyr
1                   5
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:12:

```
Ala  Ser  Ser  Leu  Pro  Thr  Thr  Met  Asn  Tyr
1                   5                        10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:13:

```
Ala  Ser  Ser  Phe  Ser  Thr  Thr  Ile  Asn  Tyr
1                   5                        10
```

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:14:

Ser  Ser  Leu  Pro  Thr  Thr  Met  Asn  Tyr
    1                      5

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:15:

Gly  Ser  Val  Val  Gly  Asn  Trp  Gln  Tyr
    1                      5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:16:

Ser  Ser  Phe  Ser  Thr  Thr  Ile  Asn  Tyr
    1                      5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:17:

Phe  Ala  Thr  Cys  Leu  Gly  Leu  Ser  Tyr
    1                      5

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:18:

Leu  Val  Thr  Cys  Leu  Gly  Leu  Ser  Tyr
    1                      5

( 2 ) INFORMATION FOR SEQ ID NO:19:

( i ) SEQUENCE CHARACTERISTICS:

```
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Leu  Gly  Ser  Val  Val  Gly  Asn  Trp  Gln  Tyr
    1                   5                        10

( 2 ) INFORMATION FOR SEQ ID NO:20:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Ile  Phe  Ala  Thr  Cys  Leu  Gly  Leu  Ser  Tyr
    1                   5                        10
```

INDUCTION OF ANTI-TUMOR CYTOTOXIC T LYMPHOCYTES IN HUMANS USING SYNTHETIC PEPTIDE EPITOPES

The present application is a continuation in part of U.S. Ser. No. 08/159,339, filed Nov. 29, 1993, now pending, which is a continuation in part of U.S. Ser. No. 08/103,396, filed Aug. 6, 1993 (now abandoned), which is a continuation in part of U.S. Ser. No. 08/027,746, Mar. 5, 1993 (now abandoned), which is a continuation in part of U.S. Ser. No. 07/926,666, filed Aug. 7, 1992 (now abandoned).

BACKGROUND OF THE INVENTION

The present invention relates to compositions and methods for preventing, treating or diagnosing cancers. In particular, it provides novel peptides capable of binding major histocompatibility complex (MHC) molecules and inducing an immune response against selected tumor cells.

The immune system has the ability to mount responses that can destroy tumor cells. Among the various elements of the immune system, cytotoxic T lymphocytes (CTL) are likely the most effective in mediating the rejection of established tumors. This is because CTL recognize antigenic determinants produced from any protein synthesized within the cell, while antibodies recognize and bind only integral cell surface molecules.

The anti-tumor activity of tumor-specific CTL is the result of a series of complex molecular events. More specifically, after cellular processing of proteins in the cytoplasm of the tumor cells, small peptides are transported to the endoplasmic reticulum, where they bind to newly synthesized major histocompatibility gene complex (MHC) class I molecules. MHC/peptide complexes are then exported to the surface of the tumor cell, where they are recognized by antigen-specific Class I-restricted CTL. In addition to lysing the tumor cell, the CTL may also secrete lymphokines such as tumor necrosis factor (TNF), and gamma-interferon (γ-IFN), which also contribute to the overall anti-tumor effect.

Mutations of genes encoding cellular proteins (such as oncogenes), and/or the overexpression of genes coding for regulatory proteins (such as, tumor suppressor proteins) can result in the production of potential tumor-specific immunogenic peptides. A family of approximately 12 genes of yet undefined function (called MAGE, for "melanoma antigen") have been described, some of which are selectively expressed in a variety of human malignant cells (particularly in melanomas), but not in most normal tissues, with the exception of the testis (WO 92/20356). For example, the MAGE-1 gene is expressed in approximately 40% of melanomas and in some other tumors. A recent report has described the isolation from a melanoma patient of CTL specific for a 9 residue peptide (EADPTGHSY) (SEQ ID NO.:1), derived from the processing of the MAGE-1 protein (van der Bruggen, et al. (1991) Science 254:1643–1647). Evidence also shows that the CTL recognize the MAGE-1-derived peptide in the context of the HLA-A1 molecule (Traversari et al. (1992) J. Exp. Med. 176:1453–457).

In contrast with the somewhat limited frequency of expression of MAGE-1, the MAGE-2 and MAGE-3 genes are expressed in approximately 80–90% of the melanoma lines examined, and also in the other tumor types such as breast, colon, lung and thyroid cancers (Zakut et al. (1990) Cancer Res. 53:5–8). Thus, it would be attractive to identify peptides derived from the MAGE-2 or MAGE-3 gene products which could serve as CTL antigens.

Despite the developments in the art, the prior art has yet to provide a useful human peptide-based vaccine or therapeutic agent based on this work. The present invention provides these and other advantages.

SUMMARY OF THE INVENTION

The present invention provides compositions comprising immunogenic peptides capable of inducing an immune response against cells expressing a protein comprising an epitope having the sequence EVDPIGHLY (SEQ ID NO.:2). The cells are usually tumor cells, such as melanoma cells expressing a protein product of the MAGE-3 gene. The peptides of the invention usually consist essentially of about 8 to about 10 residues and have the sequence EVDPIGHLY (SEQ ID NO.:2).

The immunogenic peptides can be included in pharmaceutical compositions comprising a pharmaceutically acceptable carrier and the peptides. If used as a vaccine, the compositions will typically further comprise an adjuvant. The pharmaceutical compositions are used to induce an immune response against a target cell expressing a protein comprising an epitope having the sequence EVDPIGHLY (SEQ ID NO.:2). The methods of the invention comprise contacting cytotoxic T cells with an immunogenic peptide under conditions that induce a cytotoxic T cell response against the target cell.

The methods may involve contacting the cytotoxic T cells with the immunogenic peptide in vitro and then reintroducing the activated cells into a patient with cancer, such as melanoma. Alternatively, the peptides can be used as a vaccine to induce an immune response in vivo. A combination of in vivo vaccination with adoptive transfer of activated cytotoxic T cells can also be used to induce a strong immune response.

Definitions

The term "peptide" is used interchangeably with "oligopeptide" in the present specification to designate a series of residues, connected one to the other typically by peptide bonds between the alpha-amino and carbonyl groups of adjacent amino acids. The length of oligopeptides is not critical to the invention so long as the correct epitopes are maintained. The peptides are typically less than about 30 residues in length and usually consist of between about 8 and about 20 residues, preferably 9 or 10 residues.

An "immunogenic peptide" is a peptide which comprises an allele-specific motif such that the peptide will bind the MHC allele and be capable of inducing a CTL response against a desired epitope. Thus, immunogenic peptides are capable of binding to an appropriate class I MHC molecule (e.g., HLA A1) and inducing a cytotoxic T cell response against cells which express an antigen which comprises the epitope (e.g., MAGE-3). The epitope recognized by CTLs induced by immunogenic peptides of the invention has the sequence EVDPIGHLY (SEQ ID NO.:2).

The term "motif" refers to the pattern of residues in a peptide of defined length, usually about 8 to about 11 amino acids, which is recognized by a particular MHC allele. The peptide motifs are typically different for each human MHC allele and differ in the pattern of the highly conserved residues.

The phrases "isolated" or "biologically pure" refer to material which is substantially or essentially free from components which normally accompany it as found in its native state. Thus, the peptides of this invention do not contain materials normally associated with their in situ environment, e.g., MHC I molecules on antigen presenting cells. Even where a protein has been isolated to a homogenous or dominant band, there are trace contaminants in the range of 5–10% of native protein which co-purify with the desired protein. Isolated peptides of this invention do not contain such endogenous co-purified protein.

The term "residue" refers to an amino acid or amino acid mimetic incorporated in a oligopeptide by an amide bond or amide bond mimetic.

BRIEF DESCRIPTION OF THE DRAWINGS

FIG. 1 demonstrates that peptides MAGE-3 161–169 binds HLA-A1 as well as, or better than, the previously known T cell tumor cell epitope, MAGE-1 161–169. It also shows that the corresponding peptide MAGE-2 161–169 binds HLA-A1 with an affinity at least four orders of magnitude lower than the MAGE-3 peptide.

FIG. 2A shows cytotoxic responses using peptide-loaded target cells and melanoma tumors: (●), Steinlin (HLA homozygous, Epstein-Barr Virus-transformed lymphoblastoid cell line, HLA-A1/1, −B8/8) pulsed with MAGE-3 peptide EVD-PIGHLY (SEQ ID NO.:2); (▲), Steinlin cells pulsed with MAGE-1 peptide EADPTGHSY (SEQ ID NO.:1); (○), Steinlin cells with no peptide; (▼), mel-397 (HLA-A1/25, MAGE-3+); (Δ), mel-938 (HLA-A1/24,−B7/8,MAGE-3+); (◇), mel-888 (HLA-A1/24, −B22/52, −Cw1/w7 MAGE-3-); (♦), mel-888 pulsed with MAGE-3 peptide EVDPIGHLY (SEQ ID NO.:2); (▽), mel-526 (HLA-A2/3, −B50/62, −Cw3, MAGE-3+). FIG. 2A demonstrates that CTLs induced with peptide EVDPIGHLY (SEQ ID NO.:2) can specifically kill MAGE-3-expressing melanoma tumor cells.

FIG. 2B shows cytotoxic responses using peptide-loaded HLA-mutant cells expressing single MHC class I molecules (ref. 21) (●), .221 (A1) pulsed with MAGE-3 peptide EVDPIGHLY; (○), 0.221 (A1) without peptide; (■), 0.221 (A2.1) pulsed with MAGE-3 peptide EVDPIGHLY (SEQ ID NO.:2); (□), 0.221 (A2.1) without peptide. FIG. 2B demonstrates that MAGE-3-specific CTL are restricted by HLA-A1 molecules.

FIG. 3 demonstrates that MAGE-3-specific CTL can kill tumors other than melanoma which express the MAGE-3 gene product.

DESCRIPTION OF THE PREFERRED EMBODIMENT

The present invention provides immunogenic peptides capable of inducing immune responses against tumor cells. The peptides bind desired MHC Class I molecules and induce a CTL response against tumor cells expressing proteins which comprise desired epitopes.

The results presented here show that a 9 residue peptide (EVDPIGHLY (SEQ ID NO.:2)) derived from the sequence of the MAGE-3 protein can be used to elicit a primary CTL response against cells expressing MAGE-3.

Synthetic peptides disclosed here can be used therapeutically to elicit CTL responses to melanoma, breast, colon, prostate, or other cells which express proteins (such as the MAGE-3 or MAGE-2 gene products) having the EVD-PIGHLY (SEQ ID NO.:2) epitope. This approach can be used therapeutically either in the form of a peptidic vaccine, or for ex vivo therapy in which CTL are induced in tissue culture and used for adoptive immunotherapy.

Peptide binding to MHC Class I molecules is determined by the alleic type of the MHC molecule, and the amino acid sequence of the peptide. MHC class I-binding peptides, usually contain within their sequence two conserved ("anchor") residues that interact with corresponding binding pockets in the MHC molecule. Specific combination of anchor residues (usually referred to as "MHC motifs"), required for binding by several allelic forms of human MHC (HLA, histocompatibility leukocyte antigens) are described for instance in copending applications U.S. Ser. No. 08/159, 339, U.S. Ser. No. 08/103,396, U.S. Ser. No 08/027,746 and U.S. Ser. No. 07/926.666. Definition of specific MHC motifs allows one to predict from the amino acid sequence of an individual protein, such as tumor-associated molecules, which peptides have the potential of being immunogenic for CTL.

The present invention provides particular immunogenic peptides which are derived from the sequence of the MAGE-3 gene product. Peptides bearing MHC-binding motifs for HLA-A1 were screened for their capacity to bind to purified HLA-A1 molecules. The high affinity MHC-binding peptides were studied for their ability to elicit a primary CTL responses using lymphocytes from normal donor volunteers. Using this strategy, peptides derived from the MAGE-3 sequence can be used to elicit CTL capable of killing MAGE-3+ tumor cells.

The nomenclature used to describe peptide compounds of the invention follows the conventional practice wherein the amino group is presented to the left (the N-terminus) and the carboxyl group to the right (the C-terminus) of each amino acid residue. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The immunogenic peptides can be prepared synthetically, or by recombinant DNA technology or isolated from natural sources such as tumor cells expressing the MAGE-3 gene product. Although the peptide will preferably be substantially free of other naturally occurring host cell proteins and fragments thereof, in some embodiments the peptides can be synthetically conjugated to native fragments or particles. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of 9 or 10 amino acid residues, commensurate in size with endogenously processed tumor cell peptides that are bound to MHC class I molecules on the cell surface.

As explained below, the in vivo immunogenicity of a peptide comprising the CTL epitope can be increased by modifications such as lipidation, glycosylation or conjugation to other peptides, such as those that stimulate T helper lymphocytes. For instance, covalent attachment of lipid chains such as palmitic acid to peptides will increase immunogenicity. In addition, the use of amino acid sequences in the form of synthetic peptides, protein carriers or recombinant DNA-derived products, which stimulate helper T lymphocytes will increase the CTL response to the peptide containing the CTL epitope. Specifically, an amino acid sequence containing a T helper epitope can be linked to sequence that represents the CTL epitope to create an immunogenic entity. Alternatively, a mixture of 2 or more separate entities, representing the epitopes recognized by CTL and T helper lymphocytes, can be administered to elicit the desired CTL response.

Peptides having the desired activity may be modified as necessary to provide certain desired attributes, e.g., improved pharmacological characteristics, while increasing or at least retaining substantially all of the biological activity of the unmodified peptide to bind the desired MHC molecule and activate the appropriate T cell. For instance, the peptides may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, (1986) *Science* 232:341–347, Barany and Merrifield, The Peptides, Gross and Meienhofer, eds. (New York, Academic Press), pp. 1–284 (1979); and Stewart and Young, *Solid Phase peptide Synthesis*, (Rockford, Ill., Pierce), 2d Ed. (1984).

The peptides can also be modified by extending or decreasing the compound's amino acid sequence, e.g., by the addition or deletion of amino acids. The peptides of the invention can also be modified by altering the order or composition of certain residues, it being readily appreciated that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions generally are made in accordance with the following Table 1 when it is desired to finely modulate the characteristics of the peptide.

TABLE 1

| Original Residue | Exemplary Substitution |
| --- | --- |
| Ala | Ser |
| Arg | Lys, His |
| Asn | Gln |
| Asp | Glu |
| Cys | Ser |
| Gln | Asn |
| Glu | Asp |
| Gly | Pro |
| His | Lys; Arg |
| Ile | Leu; Val |
| Leu | Ile; Val |
| Lys | Arg; His |
| Met | Leu; Ile |
| Phe | Tyr; Trp |
| Ser | Thr |
| Thr | Ser |
| Trp | Tyr; Phe |
| Tyr | Trp; Phe |
| Val | Ile; Leu |

Substantial changes in function (e.g., affinity for MHC molecules or T cell receptors) are made by selecting substitutions that are less conservative than those in Table 1, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl; (b) a residue having an electropositive side chain, e.g., lysl, arginyl, or histidyl, is substituted for (or by) an electronegative residue, e.g. glutamyl or aspartyl; or (c) a residue having a bulky side chain, e.g. phenylalanine, is substituted for (or by) one not having a side chain, e.g., glycine.

The peptides may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983).

Modifications of peptides with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., *Eur. J. Drug Metab Pharmacokin.* 11:291–302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides of the present invention which have CTL stimulating activity may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated. The T helper peptides used in the invention can be modified in the same manner as CTL peptides. For instance, they may be modified to include D-amino acids or be conjugated to other molecules such as lipids, proteins, sugars and the like.

In some embodiments, the T helper peptide is one that is recognized by T helper cells in the majority of the population. This can be accomplished by selecting amino acid sequences that bind to many, most, or all of the MHC class II molecules. These are known as "loosely MHC-restricted" T helper sequences. Examples of amino acid sequences that are loosely MHC-restricted include sequences from antigens such as Tetanus toxin at positions 830–843 (QYIKANSKFIGITE (SEQ ID NO.:5)), *Plasmodium falciparum* CS protein at positions 378–398 (DIEKKIAKMEKASSVFNVVNS (SEQ ID NO.:6)), and Steptococcus 18 kD protein at positions 1–16 (YGAVDSILGGVATYGAA (SEQ ID NO.:7)). For example, a vaccine comprising a peptide containing a MAGE-3 epitope (EVDPIGHLY (SEQ ID NO.:2)) linked at the N-terminus to a peptide comprising the tetanus toxin epitope (QYIKANSKFIGITE (SEQ ID NO.:5)) using a AAA spacer can be used. The tetanus toxin peptide is further lipidated at its N-terminus using two palmitic acid residues via a KSSAAA (SEQ ID NO.:8) spacer. This construct, which has the formula $(PAM)_2$-KSSAAAQYIKANSKFIGITEAAAEVDPIGHLY (SEQ ID NO.:9), can be used to elicit a strong tumor-specific CTL response. This general type of vaccine is described in copending application U.S. Ser. No. 07/935,811.

Alternatively, it is possible to prepare synthetic peptides capable of stimulating T helper lymphocytes, in a loosely MHC-restricted fashion, using amino acid sequences not found in nature. These synthetic compounds called Pan-DR-binding epitope (PADRE) are designed on the basis of their binding activity to most, HLA-DR (human MHC class II) molecules (see, copending application U.S. Ser. No. 08/121, 101). For instance, a peptide having the formula: aKX-VWANTLKAAa (SEQ ID NO.:10), where X=cyclohexylalanine, and a=D-alanine, has been found to bind to most HLA-DR alleles, and to stimulate the response of T helper lymphocytes from most individuals, regardless of their HLA type. T helper epitopes can also be modified to increase their biological effect. For example, peptides presenting T helper epitopes can contain D-amino acids to increase their resistance to proteases and thus extend their serum half-life. Also, the T helper peptides can be conjugated to other molecules such as lipids, proteins or sugars, or any other synthetic compound, to increase their biological activity. Specifically, the T helper peptide can be conjugated to one or more palmitic acid chains at either the amino or carboxyl termini.

In some embodiments it may be desirable to include in the pharmaceutical compositions of the invention at least one component which assists in priming CTL. Lipids have been identified as agents capable of assisting the priming CTL in vivo against various antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and-epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime tumor specific CTL when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a CTL response to the target antigen. Further, as the induction of neutralizing antibodies can also be primed with P3CSS conjugated to a peptide which displays an appropriate epitope, the two compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. Modification at the C terminus in some cases may alter binding characteristics of the peptide. In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxyl amidation, e.g., ammonia, methylamine, etc. In some instances these modifications may provide sites for linking to a support or other molecule.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982). Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent cancer. Examples of diseases which can be treated using the immunogenic peptides of the invention include melanoma, breast, colon, lung, and thyroid cancers. The expression of the MAGE-3 gene can be determined using standard techniques such as measuring the presence of MAGE-3 mRNA in the tumor cells, for example by PCR or Northern blot analysis.

In therapeutic applications, compositions are administered to a patient in an amount sufficient to elicit an effective CTL response to the tumor antigen and to cure, prevent metastases, or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by one or more boosting dosages of from about 1.0 µg to about 1000 µg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For example, the peptide EVDPIGHLY (SEQ ID NO.:2) can be used in an equimolar mixture with the PADRE peptide, aKXVWANTLKAAa (SEQ ID NO.:10), to treat HLA-A1+ cancer patients that have tumors expressing the MAGE-3 gene product. The peptide mixture is formulated into an immunogenic vaccine, for example in an emulsion with IFA, or Seppic Montanide ISA-51. The optimal CTL immunogenic dose of peptide mixture is typically in the range of 1–10000 µg of CTL peptide, preferentially between 10 and 1000 µg of peptide, for a 60–90 Kg patient. The peptide vaccine is administered repetitively ever 2–8 weeks, preferentially every 3–4 weeks, to boost the CTL response. The number of boosts can range from 1–10, preferentially 2–4, depending on the therapeutic effect of the vaccine. The therapeutic effect of the vaccine is evaluated, for instance, by determining the disappearance, shrinkage, or reduction in number of tumor masses. In addition, the effect can also be measured by prevention of the establishment of metastasis, by determining the establishment of new tumor masses. This effect can be correlated by the presence, or increase of MAGE-3-specific CTL during and after vaccination.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, ISCOMS, slow-releasing particles and the like to increase immunogenicity and/or serum half life of the peptides. For instance, liposomes can be used to target the peptides to a particular tissue, such as lymphoid tissue, or targeted selectively to infected cells, as well as increase the half-life of the peptide composition. Liposomes include emulsions, foams, micelies, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, for example, Szoka et al., *Ann. Rev. Biophys. Bioeng.* 9:467 (1980), U.S. Pat. Nos. 4,235,871, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as bovine serum albumin, tetanus toxoid, polyamino acids such as poly(lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as complete or incomplete Freund's adjuvant, Montanide ISA-51 (Seppic, Inc., Fairfield, N.J.), aluminum phosphate, aluminum hydroxide, alum, saponin, various bacterially derived products and the like can be used. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Alternatively, peptides of the invention can be incorporated into professional antigen-presenting cells (APC), such as dendritic cells, in order to formulate an immunogenic CTL vaccine. Another way to enhance the immunogenic activity of a peptide containing a CTL epitope is the use of soluble cell-derived factors known as cytokines, which are known to participate in the regulation of immune responses. For example interleukin-2, (IL-2) IL-7, and IL-12 are known to enhance CTL responses. Specifically, the peptide vaccine could be administered together with an optimal dose of IL-2, IL-7 IL-12, or any other cytokine, to potentiate the CTL response to a CTL peptide of the invention.

Vaccine compositions containing the peptides of the invention are administered to a patient susceptible to or otherwise at risk of cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg mg per 70 kg of body weight.

For therapeutic or immunization purposes, the peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

Antigenic peptides may be used to elicit CTL ex vivo, as well. The resulting CTL, can be used to treat tumors in patients that do not respond to other conventional forms of therapy, or will not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate immunogenic peptide. In order to optimize the in vitro conditions for the generation of specific cytotoxic T cells, the culture of stimulator Cells is maintained in an appropriate serum containing or serum-free medium. Various cytokines (either recombinantly produced or naturally occurring) known to enhance CTL response are also used in the incubation medium. Examples include, IL-1, IL-2, IL-6, IL-7, and IL-12. Appropriate APC include autologous peripheral blood mononuclear cells (PBMC), preferably "professional" antigen presenting cells such as dendritic cells, macrophages, and activated B cells.

After an appropriate incubation time (typically 1–4 weeks) and the expansion of the antigen specific CTL to high numbers (for example, from $10^7$ to $10^{11}$), the cells are infused back into the patient, where they will destroy their specific target tumor cell. The infusion of CTL into cancer patients can be done together with the administration of cytokines that will enhance the in vivo effect of the CTL. For example administration of IL-2 and/or IL-4 together with the CTL will prolong the survival and allow further expansion of the CTL in vivo. The number of CTL infusions can be between 1–10, preferentially between 2 and 5 depending in the therapeutic effect of this treatment.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 400 or more, human Class I MHC molecules loaded with peptide to be expressed on the surface of each stimulator cell. Preferably, the stimulator cells are incubated with >20 μg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatibility complex molecules on cells allows the induction of primary cytotoxic T lymphocyte responses. Peptide loading of empty major histocompatibility complex molecules on cells enables the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. Methods for stripping the endogenous MHC-associated peptides from the surface of APC followed by the loading of desired peptides are described below.

A stable MHC class I molecule is a trimeric complex formed of the following elements: 1) a peptide usually of 8–10 residues, 2) a transmembrane heavy polymorphic protein chain which bears the peptide-binding site in its α1 and α2 domains, and 3) a non-covalently associated non-polymorphic light chain, $\beta_2$microglobulin. Removing the bound peptides and/or dissociating the $\beta_2$microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destablize $\beta_2$microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty Surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class ii molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$–$5\times10^7$ cells used in mice.

Preferably, as discussed above, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The immunogenic peptides of this invention may also be used to make monoclonal antibodies. Such antibodies may be useful as potential diagnostic or therapeutic agents.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

The following examples are offered by way of illustration, not by way of limitation.

EXAMPLE

MATERIALS AND METHODS

Synthetic Peptides. Peptides used for MHC binding assays were purchased from Chiron/Mimotopes (Clayton, Victoria, Australia). For cellular assays, synthetic peptides were prepared on an Applied Biosystems machine (Foster City, Calif.). Briefly, after removal of the α-amino-ter-butylocarbonyl protecting group, the phenylacetamidom-ethyl resin peptide was coupled with a 4 fold excess of preformed symmetrical anhydride (hydroxybenzyltriazole esters for arginine, histidine, asparagine, and glutamine) for 1 hr in dimethylformamide. For arginine, histidine, asparagine, glutamine and histidine residues, the coupling step was repeated in order to obtain a high efficiency coupling. Peptides were cleaved by treatment with hydrogen fluoride in the presence of the appropriate scavengers. Synthetic peptides were purified by reverse phase high pressure liquid chromatography. The purity of the peptides, which was routinely >95% was determined by amino acid sequence and/or composition analysis.

Purification of HLA-A1 Molecules. For the peptide-MHC binding assays the HLA-A1 molecules were purified using a procedure similar to the one described in Ruppert, et al. (1993) *Cell*, 74:929–937, except that Steinlin cells (HLA-A1 homozygous) were used as a source of MHC molecules. Briefly, detergent extracts of Steinlin cells were first depleted of HLA-B and -C antigens by repeated passage over a column prepared with monoclonal antibody B1.23.2, which is specific for these molecules (Rebai, et al. (1983) *Tissue Antigens* 22:107–117). HLA-A1 molecules were subsequently purified by affinity chromatography using an immunoadsorbent prepared with antibody W6/32, which recognizes all human MHC class I molecules associated to β2-microglobulin (Barnstable et al. (1978) *Cell* 14:9–20). The adsorbed HLA-A1 molecules were eluted from the column with base (50 nM diethylamine) containing 1% octyl glucoside. The eluted HLA-A1 molecules were neutralized and dialyzed against PBS containing PBS octyl glucoside, and concentrated by ultrafiltration. Protein purity was determined by SDS-PAGE.

MHC Binding Assay. Peptide binding to class I MHC molecules was measured using standard techniques. Briefly, the peptide binding assay to purified MHC class I molecules is based on the inhibition of binding of the radiolabeled standard peptide, $^{125}$I-YLEPAIAKY (SEQ ID NO.:3) to detergent solubilized MHC molecules. The standard peptide was radioiodinated using $^{125}$I (ICN, Irvine, Calif.) by the chloramine T method. HLA-A1 concentrations yielding approximately 15% of bound peptide (approximately in the 10 nM range) were used in the inhibition assays. Various doses of the test peptides (10 μM to 1 nM) were incubated together with 5 nM radiolabeled standard peptide and HLA-A1 molecules for 2 days at room temperature in the presence of a cocktail of protease inhibitors and 1 μM β2-microglobulin (Scripps Labs., San Diego, Calif.). At the end of the incubation period, the % MHC bound radioactivity was determined by gel filtration.

Cell Lines. The Steinlin cell line (HLA-A1/1, –B8/8) was obtained from the American Society for Histocompatibility and Immunogenetics (ASHI) Cell Repository (Brigham and Women's Hospital, Boston, Mass.). The HLA-typed melanoma cell lines were provided by S. Rosenberg, National Cancer Institute, NIH, Bethesda, Md. The breast carcinoma lines HBL-100 and BT-20, and the prostate cancer line PC3 were obtained from the American Type Tissue Collection (Rockville, Md.).

The 0.221(A1) and 0.221(A2.1) cells were produced by transferring the HLA-A1 and -A2.1. genes into the HLA-A, -B, -C-null mutant human B lymphoblastoid cell line 0.221 (Shimizu, et al. (1989) *J. Immunol* 142:3320–3328). The HLA genes were first removed from their pHeBo vectors and cloned into the RSV.5 neo vector (Long et al. (1991) *Hum. Immunol.* 31:229–235) for the production of stably transformed cells. After transfer of the plasmids into 0.221 cells, the 0.221 (A1) and 0.221 (A2.1) clones were isolated by selection in medium containing 400 µg/ml G418 (Sigma, St. Louis, Mo.). Flow cytometry of anti-class I MHC antibody binding showed that 0.221 (A1) and 0.221 (A2.1) cells express 50–100% as much as cell surface HLA-A molecules as do normal lymphoblastoid cells expressing single copies of the same HLA alleles in their native chromosomal locations.

All tumor lines were maintained in culture using RPMI-1640 medium supplemented with antibiotics and 10% (V/V) FBS (and 400 µg/ml G418 for the 0.221 (A1) and 0.221 (A2.1) cell lines). Some cells were treated with 100 U/ml γ-IFN (Genzyme) for 72 hr at 37° C. before testing their susceptibility to lysis by the CTL. In all cases, the γ-IFN-treated cells increased the level of MHC class I expression by 2–3 fold.

Primary CTL Induction Using Synthetic Peptides. CTL were elicited using synthetic peptides in normal blood donor volunteers. Informed consent for blood donations was obtained from all volunteers. Peripheral blood mononuclear cells (PBMC) from a normal volunteer (HLA-A1/24, –B8/ 38, –Cw7) were purified by centrifugation in Ficoll-Paque (Pharmacia, Piscataway, N.J.). Non-transformed lymphoblasts were used as antigen-presenting cells (APC) and were prepared by incubation of PBMC in tissue culture for 4–6 days with *Staphylococcus aureus* Cowan-I (SAC-I, Pansorbin, Calbiochem, San Diego, Calif.) at 0.005% (V/V) and 20 µl/ml rabbit antihuman IgM antibody coupled onto a solid phase (Immunobeads, BioRad, Richmond, Calif.) with 20 ng/ml recombinant IL-4 (Sandoz, Basel, Switzerland).

SAC-I-induced lymphoblasts were incubated overnight at 6° C. and were loaded with peptide at 50 µg/mi in the presence of 3 µg/ml B2-microglobulin for 4 hours at 20° C. These APC were γ-irradiated with 6,000 rads and mixed at a ratio of 1:3 with autologous CD4$^+$ cell-depleted PBMC (responder cells).

The cultures were maintained in RPMI-1640 medium (Gibco, Grand Island, N.Y.) supplemented with 5% (V/V) heat-inactivated AB human serum and 10 ng/ml recombinant IL-7 (Genzyme, Cambridge, Mass.), for 12 days at 37° C. in a 5% $CO_2$ incubator. Recombinant interleukin-2 (IL-2, Sandoz), was added to the cultures at 10 IU/ml on day 12–14. The responder cells were re-stimulated every 7–10 days with autologous-irradiated adherent cells pulsed for 2 hr with peptide (10 µg/ml). The cultures were fed every 3–5 days with fresh medium containing rIL-2. Cytotoxicity was first tested after 2 rounds of antigenic stimulation (day 19). Cytolytic activity of the T-cell line increased after every restimulation.

CTL Cytotoxicity Assays. Adherent target cells were detached from tissue culture flasks with I mM EDTA in $Ca^{++}/Mg^{++}$-free phosphate buffered saline (PBS). All cells were labeled with 100 µCi $^{51}Cr(ICN)$ per $10^6$ cells for 1 hr at 37° C. Peptide-pulsed targets were prepared incubating the cells ($10^6$) with 10 µg/ml synthetic peptide either for 1 hr (during the $^{51}Cr$ labeling) or overnight at 37° C. Target cells were washed by centrifugation and mixed with various numbers of effectors in a final volume of 0.2 ml of RPMI-1640 containing 10% fetal bovine serum (FBS, GIBCO) in round-bottom microtiter plates. After 4–6 hr incubation time, the plates were centrifuged (5 min at 400× g), and 0.1 ml of the supernatant was removed from each well, and the radioactivity was determined in a γ-counter. % Specific Cytotoxicity was determined by calculating the % Specific $^{51}Cr$ release by the formula: [(cpm of the test sample–cpm of the spontaneous $^{51}Cr$ release)/(cpm of the maximal $^{51}Cr$ release–cpm of the spontaneous $^{51}Cr$ release)]×100. The spontaneous $^{51}Cr$ release was determined by incubating the targets alone, in the absence of effectors, and the maximal $^{51}Cr$ release was obtained by incubating the targets with 0.1% Triton X-100 (Sigma Chem. Co., St. Louis, Mo.). All determinations were done in duplicates, and the standard error of the means were always below 10% of the value of the mean.

Identification of Peptides from MAGE-2 and -3 gens products that Bind to HLA-A1. Initially, the known sequences of MAGE-2 and -3 gens products were screened for peptides containing the anchor motif for HLA-A1 (T/S/M in position 2, or D/E/A/S/T in position 3, and Y in the carboxyl-terminal end, see, U.S. Ser. No. 08/159,339). A total of 10 peptides (7 from MAGE-3 and 3 from MAGE-2) of either 9 or 10 residues in length were found to contain the binding motif for HLA-A1. These peptides were synthesized and tested for binding to purified HIA-A1 molecules.

The results from the binding assay'showed that the relative binding affinities of these peptides to HLA-A1 of the peptides ranged over 4 orders of magnitude (Table 2). It was found that 2 peptides, both from MAGE-3, bound to HLA-A1 with high affinity (<than 50 nM required to achieve 50% inhibition), 3 peptides were intermediate HLA-A1 binders (50–500 nM required for 50% inhibition), while the remaining 5 peptides bound HLA-A1 only weakly (500 nM to 50 µM to achieve 50% inhibition).

Figure 1:
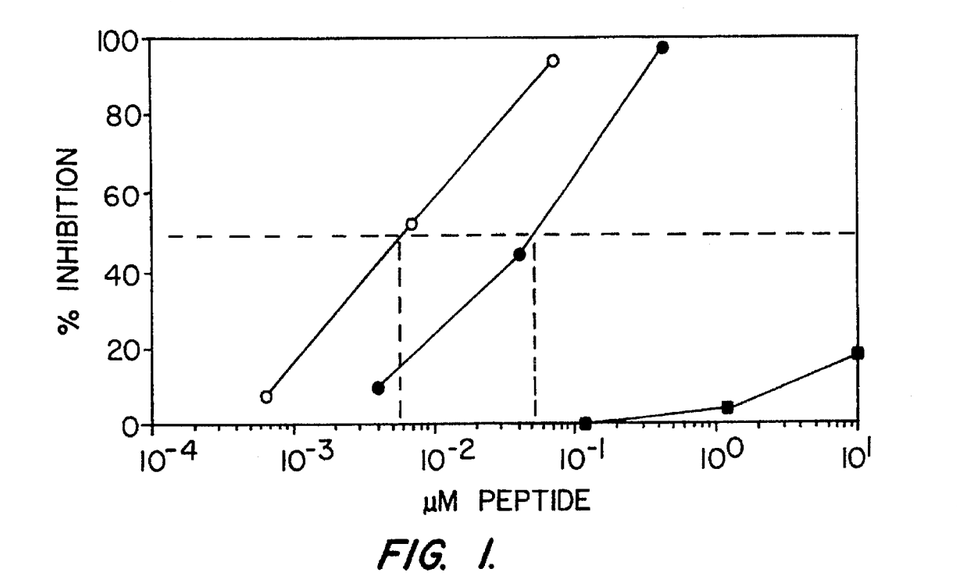
FIG. 1 shows HLA-A1 binding of synthetic peptides from MAGE-1, -2 and -3. The MAGE peptides were tested in a dose titration for the inhibition of the binding of the radiolabeled standard peptide $^{125}$I-YLEPAIAKY (SEQ ID NO.:3) to purified HLA-A1 molecules. (●), MAGE-1 peptide EADPTGHSY (SEQ ID NO.:1); (■), MAGE-2 peptide EVVPISHLY (SEQ ID NO.:4): (○), MAGE-3 peptide EVDPIGHLY (SEQ ID NO.:2). Dotted lines are used to calculate the 50% inhibitory dose for each peptide.

FIG. 1 shows a comparison of the binding capacity of the 3 peptides derived from homologous regions of the different products derived from MAGE-1, -2 and -3 genes. The data indicate that both the MAGE-1-derived peptide EADPT-GHSY (SEQ ID NO.:1) and the peptide derived from MAGE-3, EVDPIGHLY (SEQ ID NO.:2) bound with high affinity to HLA-A1. On the other hand, the peptide derived from the homologous region of MAGE-2, EVVPISHLY (SEQ ID NO.:4), which does not contain one of the anchor residues (D in position 3) bound very poorly (10,000 fold less than the others) to purified HLA-A1.

Figure 2A:
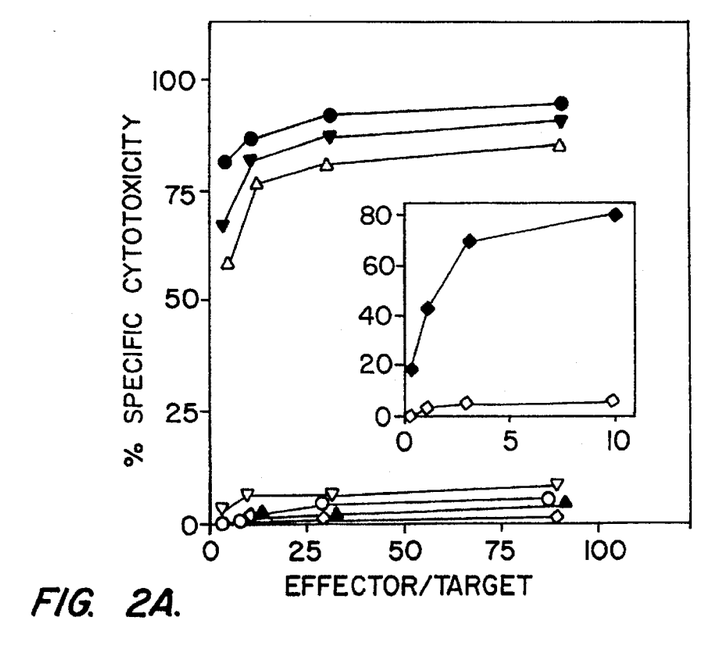
FIGS. 2A and 2B show antigen-specificity and MHC-restriction analysis of MAGE-3-reactive CTL.

Induction of Primary CTL Responses to MAGE-2 and -3 Derived Peptides. Previous observations have revealed that over 95% of the peptides corresponding to known CTL epitopes, belong to the high or intermediate MHC binding groups. Following this rationale, the 6 highest MHC-binding peptides from MAGE-2 and -3 were studied for effectiveness in raising HLA-A1-restricted CTL. Using the in vitro primary CTL induction protocol described above, PBMC were stimulated from at least 2 normal HLA-A1 volunteers with the synthetic peptides. Out of the 6 peptides studied only one, the highest MHC binder (EVDPIGHLY (SEQ ID NO.:2)), from MAGE-3 was able to elicit CTL in one of the blood donors. After 2 rounds of stimulation in culture with autologous antigen-presenting cells (APC) pulsed with peptide EVDPIGHLY (SEQ ID NO.:2), significant cytotoxic activity towards peptide-sensitized, HLA-A1-bearing target cells was observed (FIG. 2a). More significant was the observation that two MAGE-3 -expressing HLA-A1 melanoma cell lines (397-mel and 938-mel, Zakut et al. (1990) *Cancer Res.* 53:5–8) were also killed by these CTL (FIG. 2a). No anti-peptide or anti-tumor reactivities were detected in the case of the remaining 5 potential CTL epitopes, despite their screening in at least four independent HLA-A1+ blood donors.

Antigen Specificity and MHC Restriction Analysis. The CTL response appeared to be specific and HLA-A1-restricted, since HLA-A1 melanoma cells negative for MAGE-3 (mel-888), and melanoma cells that expressed MAGE-3, but of a different HLA-A allelic type (mel-526, HLA-A2/A3 Zakut et al., supra) were not lysed by the CTL line. The exogenous addition of the peptide EVDPIGHLY to the MAGE-3-negative, HLA-A1-positive mel-888 cell line rendered the cells susceptible to lysis by the CTL (FIG. 2a, insert), indicating that this tumor expresses functional HLA-A1 molecules and can function as a CTL target. Furthermore, the CTL line did not cross-react with the product of the MAGE-1 gens since it failed to kill HLA-A1 targets loaded with peptide EADPTGHSY (SEQ ID NO.:1) derived from the MAGE-1 sequence (FIG. 2a). On the basis of these data, it is evident that one or more of the 3 amino acids that are different between EYDPIGHLY (SEQ ID NO.:11) and EADPTGHSY (SEQ ID NO.:1) (at positions 2, 5 and 8) function as T-cell receptor contact residues.

Figure 2B:
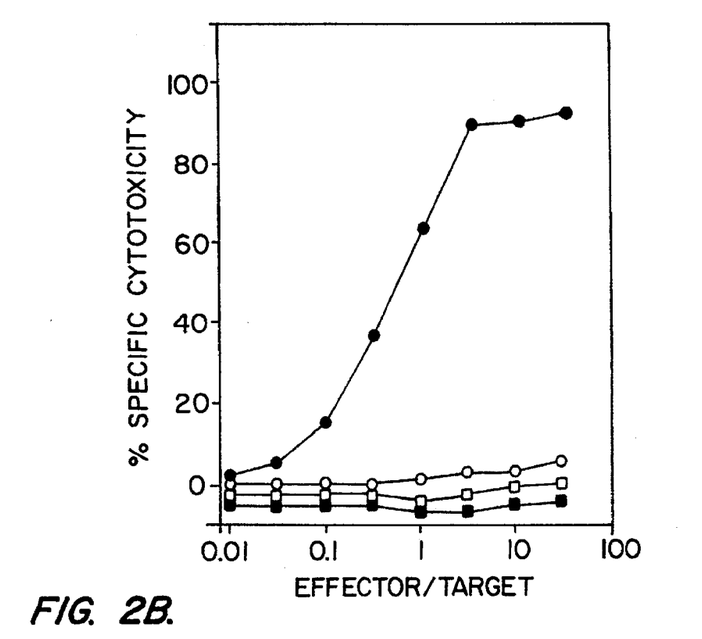

Supporting the conclusion that the restriction element for the recognition of peptide EVDPIGHLY (SEQ ID NO.:2) was HLA-A1, were results obtained using targets derived from mutant MHC class I-negative cell lines which were transfected with and express individual HLA-A (A1 or A2.1) genes. Only peptide-pulsed HLA-A1-transfected targets were killed by the CTL, but not those expressing HLA-A2.1 molecules (FIG. 2b). The MAGE-3 specific CTL line was found to express the CD3 and CD8 T-cell surface makers, typically found on most MHC class I-restricted CTL, and antibodies to the CDS molecule were found to inhibit completely the cytotoxic function of the T cell line (data not shown).

Figure 3:
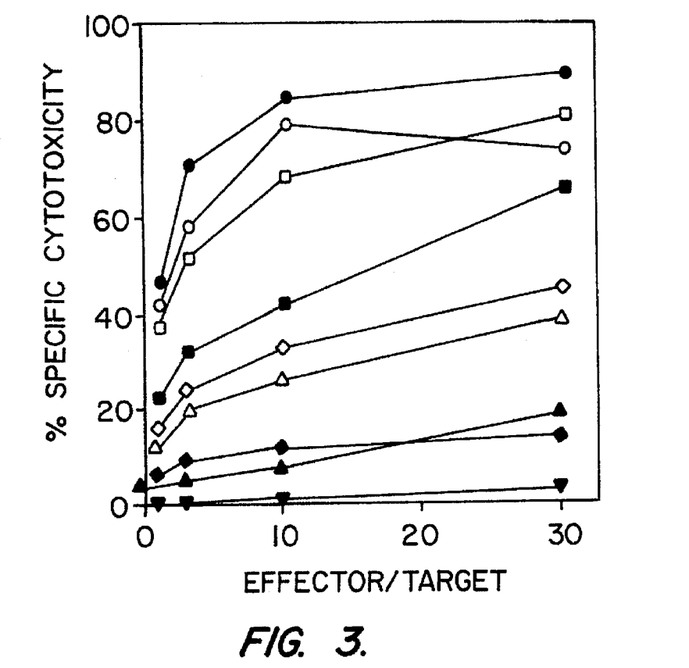
FIG. 3 shows cytotoxic activity of MAGE-3-specific CTL towards various tumors. The MAGE-3 specific CTL was tested for its ability to kill breast and prostate HLA-A1+ tumor lines previously treated, or not, with γ-IFN. Cytotoxic responses were measured against: (●), mel-397 MAGE-3+); (○), mel-397 plus, γ-IFN; (■) HBL-100 (HLA-A1/10, −B7/8 MAGE-3+); (□) HBL-100 plus γ-IFN; (▲), BT-20 (HLA-A1, −B16.MAGE-3+); (Δ), BT-20 plus γ-IFN; (■), PC3 HLA-A1/9; (◇), PC3 plus γ-IFN; (▼) mel-888 plus γ-IFN (MAGE-3−).

Cytolytic Activity to Non-Melanoma Tumors. As mentioned above, other tumors besides melanomas can also express MAGE genes, in particular MAGE-2 and -3. The ability of the MAGE-3- specific CTL line to kill HLA-A1-expressing breast and prostate carcinoma cell lines was also tested. The results in FIG. 3 show that one of the two breast cancer cell lines (HBL-100), reported to express MAGE-3 (Zakut et al., supra), was highly susceptible to lysis by the CTL. The level of lysis improved significantly if these cells were previously incubated with τ-IFN (FIG. 3), which increased (2–3 fold) the expression of MHC class I molecules on the cell surface. The other breast cancer cell line (BT-20), also reported to express MAGE-3 (Zakut et al., supra), and the prostate cancer line (PC3) were also killed, but to a lesser extent, and only when previously incubated with τ-IFN.

TABLE 2

HLA-A1 binding capacity of motif containing 9-mer and 10-mer peptides derived from the sequence of MAGE-2 and -3.

| Source | Position* | Sequence | Size | Binding IC50, nM‡ |
|---|---|---|---|---|
| MAGE-3 | 161 | EVDPIGHLY (SEQ ID NO.:2) | 9 | 4.6 |
| MAGE-3 | 61 | ASSLPTTMNY (SEQ ID NO.:12) | 10 | 9.6 |
| MAGE-2 | 61 | ASSFSTTINY (SEQ ID NO.:13) | 10 | 147.1 |
| MAGE-3 | 62 | SSLPTTMNY (SEQ ID NO.:14) | 9 | 454.6 |
| MAGE-3 | 130 | GSVVGNWQY (SEQ ID NO.:15) | 9 | 500.0 |
| MAGE-2 | 62 | SSFSTTINY (SEQ ID NO.:16) | 9 | 581.4 |
| MAGE-3 | 171 | FATCLGLSY (SEQ ID NO.:17) | 9 | 657.9 |
| MAGE-2 | 171 | LVTCLGLSY (SEQ ID NO.:18) | 9 | 2976.2 |
| MAGE-3 | 129 | LGSVVGNWQY (SEQ ID NO.:19) | 10 | 12500.0 |
| MAGE-3 | 170 | IFATCLGLSY (SEQ ID NO.:20) | 10 | 12500.0 |

*Refers to residue number of the first position of the peptide in relation to the sequence of the entire gene product.
‡Concentration of the peptide necessary to inhibit 50% binding of the radiolabeled test peptide to purified HLA-A1 molecules.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition comprising: a helper peptide having a T helper epitope, and an immunogenic peptide having the sequence EVDPIGHLY (SEQ. ID. No.2).

2. A pharmaceutical composition comprising: a pharmaceutically acceptable carrier, a helper peptide comprising a T helper epitope, and an immunogenic peptide having the sequence EVDPIGHLY (SEQ. ID. NO.2).

3. The composition of claim 2, further comprising an adjuvant.

4. The method of claim 3, wherein the adjuvant is incomplete Freund's adjuvant.

5. The method of claim 3, wherein the adjuvant is Seppic Montanide ISA-51.

6. The composition of claim 2, wherein the helper peptide is lipidated.

7. The composition of claim 6, wherein the lipid is palmitic acid.

8. The composition of claim 6, wherein the T helper epitope is QYIKANSKFIGITE (SEQ ID NO.:5).

9. The composition of claim 6, wherein the T helper epitope is aKXVWANTLKAAa (SEQ ID NO.:10).

10. The composition of claim 2, wherein the helper peptide comprising a T helper epitope and the immunogenic peptide having the sequence EVDPIGHLY (SEQ ID NO:2) are linked.

11. The composition of claim 10, wherein the T helper epitope is QYIKANSKFIGITE (SEQ ID NO.:5).

12. The composition of claim 10, wherein the T helper epitope is aKXVWANTLKAAa (SEQ ID NO.:10).

13. The method of inducing an immune response against a target tumor cell expressing an HLA-A1 molecule and a MAGE-3 protein, the method comprising contacting cytotoxic T cell with an immunogenic peptide having the sequence EVDPIGHLY (SEQ. ID. No.2) under conditions that induce a cytotoxic T cell response against the target cell.

14. The method of claim 13, wherein the cytotoxic T cells are contacted with the immunogenic peptide in vitro.

15. A method of inducing an immune response against a MAGE-3-expressing tumor cell in a patient having an HLA-A1 allele, the method comprising repetitively administering to the patient a composition comprising an equimolar mixture of an immunogenic peptide having a sequence EVDPIGHLY (SEQ ID No:2) and a peptide having a sequence aKXVWANTLKAAa (SEQ ID No:10) in an amount to induce the immune response.

16. The method of claim 15, wherein the composition is administered at least five times.

17. The method of claim 15, wherein the composition is administered at least ten times.

18. The method of claim 13, further comprising contacting the cytotoxic T cells with a peptide comprising a T helper epitope.

19. The method of claim 18, wherein the peptide comprising a T helper epitope is lipidated.

20. The method of claim 19, wherein the lipid is palmitic acid.

21. The method of claim 18, wherein the T helper epitope is QYIKANSKFIGITE (SEQ ID NO:5).

22. The method of claim 18, wherein the T helper epitope is aKXVWANTLKAAa (SEQ ID NO:10).

23. The method of claim 18, wherein the immunogenic peptide is linked to the peptide comprising a T helper epitope.

* * * * *